United States Patent [19]  [11] Patent Number: 5,231,004
Warren, III et al.  [45] Date of Patent: Jul. 27, 1993

[54] USE OF HEME-CONTAINING PROTEINS AS STABILIZERS FOR ENZYME-LABELED IMMUNOREACTANTS

[75] Inventors: Harold C. Warren, III, Rush; Bradley P. Boyer, Rochester, both of N.Y.

[73] Assignee: Eastman Kodak Company, Rochester, N.Y.

[21] Appl. No.: 522,441

[22] Filed: May 11, 1990

[51] Int. Cl.⁵ ............... G01N 33/571; G01N 33/53; G01N 33/563

[52] U.S. Cl. ............... 435/7.36; 435/7.9; 435/7.92; 435/28; 435/962; 435/975; 435/7.95; 436/510; 436/512; 436/818; 436/826

[58] Field of Search ......... 435/7.36, 7.92, 7.94, 435/7.95, 962, 975, 7.9, 188; 436/510, 511, 512, 814, 818, 826

[56] References Cited

U.S. PATENT DOCUMENTS

| | | | |
|---|---|---|---|
| 4,218,335 | 8/1980 | Mochida et al. | 252/408 |
| 4,340,668 | 7/1982 | Hornby et al. | 435/7 |
| 4,397,960 | 8/1983 | Moussebois et al. | 436/512 |
| 4,623,618 | 11/1986 | Rokugawa | 435/6 |
| 4,729,956 | 3/1988 | Hopkins | 435/188 |
| 4,828,983 | 5/1989 | McClune | 435/7 |
| 5,017,474 | 5/1991 | McClune et al. | 435/7.5 |
| 5,032,504 | 7/1991 | Mauck | 435/7.36 |

FOREIGN PATENT DOCUMENTS 2631125 11/1989 France ............... 435/7.36

OTHER PUBLICATIONS

Chemicon Monoclonal Antibodies and Immunological Reagents, (pp. 25 and 39), 1989.
Vellacott et al., Lancet, 1: pp. 18-19, (Jan. 3, 1981).
Voller et al., "Chapter 17—Enzyme-Linked Immunosorbent Assay", Manual of Clinical Laboratory Immunology, 3rd Ed., Rose et al., editors, pp. 99-109 (1986).

Primary Examiner—Esther L. Kepplinger
Assistant Examiner—Carol E. Bidwell
Attorney, Agent, or Firm—J. Lanny Tucker

[57] ABSTRACT

Heme-containing proteins, such as cytochrome c, are useful in admixture with enzyme-labeled immunoreactants, such as peroxidase-labeled antibodies or fragments thereof. The heme-containing proteins and enzyme-labeled immunoreactants can be supplied in a buffered composition as part of a test kit. The buffered composition comprising the heme-containing protein and peroxidase-labeled immunoreactant excludes 4'-hydroxyacetanilide, which is a phenolic electron transfer agent. The composition can be used in immunoassays for detecting various immunologically reactive species, such as hCG, and chlamydial or gonococcal antigens.

15 Claims, 1 Drawing Sheet

USE OF HEME-CONTAINING PROTEINS AS STABILIZERS FOR ENZYME-LABELED IMMUNOREACTANTS

FIELD OF THE INVENTION

This invention relates to a buffered composition and a test kit including same. It also relates to the use of this composition in a variety of immunological methods for the detection of various immunologically reactive ligands. Such methods allow for the detection of various medical conditions, or for diagnosis and treatment of various diseases.

BACKGROUND OF THE INVENTION

There is a continuous need in medical practice, research and diagnostic procedures for rapid and accurate determinations of biological substances which are believed or known to be present in biological fluids. For example, the presence of drugs, narcotics, hormones, steroids, polypeptides, proteins, polysaccharides, prostaglandins or infectious organisms in blood, saliva, semen, vaginal secretions, urine, tissue cultures and other biological fluids and specimens has to be determined in a rapid and efficient manner for suitable diagnosis and treatment at a cost that is not prohibitive.

To provide such determinations, various methods have been devised for isolating and detecting the presence of a biological or chemical substance which participates in an immunological reaction, such as an antibody or antigenic material, drug or hapten. Such substances are identified herein as "immunoreactants", and biological or chemical substances which specifically bind (or react) with them to form an immunological complex are identified herein as "receptors". Often, one or the other reactants in such a complex, or even a third substance reactive with either of the first two reactants, is labeled with a detectable marker to provide a means for detecting the complex. Radioisotopes, enzymes, chemiluminescent moieties, fluorescent moieties and dyes have been generally used for this purpose.

Immunoassays have been growing in importance in recent years as a means for detecting the presence or amount of infectious agents in animals or humans. Generally, the infectious agent is detected by determining the presence or amount of an immunological complex formed from an antigenic component extracted therefrom, or by determining the presence or amount of antibodies to the infectious agent in a specimen.

In recent years, the use of enzyme labels has received increasing attention because they provide distinct advantages over other labels, particularly radioisotopes and fluorescent markers. Enzyme labels are becoming prominently used in immunoassays for detecting infectious agents in what are known in the art as competitive enzyme immunoassays (EIA), both direct and indirect enzyme linked immunosorbent assays (ELISA), and immunometric or "sandwich" assays.

One such infectious agent which can be detected by immunoassays is *Chlamydia trachomatis* (herein *C. trachomatis*) which is one of two microbial species of the genus Chlamydiaceae, order Chlamydiales. There are 15 or more strains of this species which are the causes of a number of human ocular and genital diseases including trachoma, inclusion conjunctivitis, *lymphogranuloma venereum*, nongonococcal urethritis and proctitis. Infection from *C. trachomatis* is pervasive in the general population so that it is believed that there are millions of cases each year of nongonococcal urethritis alone.

Gonorrhea is another disease usually transmitted by sexual contact, and is caused by a bacterium of the Neisseria genus, especially *N. gonorrhoeae*. The disease has plagued mankind for thousands of years, and although antibiotics have helped control its spread, it still persists in epidemic proportions in many parts of the world. The importance of detection and treatment of this organism is well recognized. *N. meningitidis* and *N. lactamica* are also species of considerable medical and diagnostic interest.

Because of the widespread nature of these diseases, there is considerable interest in having a rapid, simple and reliable test for detection of chlamydial and gonococcal organisms. Considerable research has been carried out to find useful ways to extract and detect antigens from chlamydial and gonococcal organisms.

Assays for *C. trachomatis* and *N. gonorrhoeae* carried out using a solid support are described in U.S. Pat. No. 4,497,899 and U.S. Pat. No. 4,497,900, respectively (both issued Feb. 5, 1985 to Armstrong et al and Abram et al, respectively). The described assays are performed by extracting antigen from the organism and coating it on a bare solid support. The coated antigen is then detected with either one or two antibodies, one of which is suitably labeled with an enzyme. The critical feature of the assays appears to be the use of a solid support for attachment which is untreated or uncoated with any biological material. Attachment of antigen is apparently achieved by incubating the coated support for an extended time sufficient to cause adsorption of antigen thereon. The absorption time is at least 30 minutes at elevated temperature (37° C.). The entire assay described in U.S. Pat. No. 4,497,899 takes at least 3 hours to perform. A similar quicker assay is described in U.S. Pat. No. 4,497,900 for *N. gonorrhoeae*.

It would be desirable to have a much more rapid test for chlamydial or gonococcal organisms which has high reliability and can be performed at room temperature.

Such an improvement is described and claimed in copending U.S. Ser. No. 255,923 (filed Oct. 7, 1988 by Pronovost) now U.S. Pat. No. 5,075,220 (issued Dec. 24, 1991). It was found that ionically charged supports attract chlamydial or gonococcal antigen and enable one to quickly and sensitively detect such antigens. However, further improvements were needed for some biological specimens, especially those containing copious amounts of whole blood, mucus or components. Thus, the improvement described in copending U.S. Ser. No. 255,920 (filed Oct. 7, 1988 by Mauck) now U.S. Pat. No. 5,032,504 (issued Jul. 16, 1991) was made.

Despite the considerable improvements described in the copending applications noted above, there is a continued need to make the assay faster (that is, less than 20 minutes). It would be desirable to eliminate as many steps as possible from the earlier assay protocols so users would find the assays more convenient and suitable for prompt diagnosis and treatment of chlamydial and gonococcal infections. Moreover, the peroxidase-labeled antibody conjugate used in the known assays has a certain degree of stability (and thus, shelf life), but there is a need for additional stability and longer shelf life.

A highly rapid and accurate assay is described in more detail in copending U.S. Ser. No. 522,444 (filed on even date herewith by Mauck, Boyer, Warren III, Sprague and Snodgrass) and entitled "Use of Enzyme- Labeled Antibody Fragment in Determination of Chlamydial or Gonococcal Antigens". In this assay, increased rapidity of the assay is achieved because fewer steps are employed to detect the antigen. Moreover, an enzyme-labeled antibody F(ab')$_2$ fragment was found to be more stable than an enzyme-labeled whole antibody.

However, in developing that assay, which solved a number of problems with known assays, it was found that premature reaction of the enzyme-label (particularly, peroxidase) conjugated to antibody fragments produced unwanted background which obscured true positive signals in assays. This was particularly found to be a problem with the negative controls which were used to indicate whether the assay protocol was properly carried out. Although it is presently uncertain, it is speculated that the enzyme label on the antibodies may be involved in a reaction with residual substrate (that is, hydrogen peroxide when the enzyme is peroxidase) and phenolic electron transfer agents (such as 4'-hydroxyacetanilide) which are often used to enhance the rate of dye formation in the presence of the enzyme (see for example U.S. Pat. No. 4,828,983, issued May 9, 1989 to McClune). The result is unwanted dye formation.

Stable compositions of enzyme-labeled immunoreactants such as antibodies or antibody fragments are needed to provide rapid assays without undesirable background signal.

SUMMARY OF THE INVENTION

The problems noted above were solved with the use of a buffered composition comprising an enzyme-labeled immunoreactant in admixture with a heme-containing protein, but excluding 4'-hydroxyacetanilide.

This composition can be supplied as part of a test kit useful for the determination of an immunologically reactive ligand, the kit comprising:

a. the buffered composition described above wherein the enzyme-labeled immunoreactant is a receptor for the ligand, and b. a dye-providing composition which provides a dye in the presence of the enzyme label.

Moreover, this invention provides a method for the determination of an immunologically reactive ligand comprising:

A. contacting an immunologically reactive ligand of interest with the buffered composition described above wherein the enzyme-labeled immunoreactant is a receptor for the ligand of interest, so as to form an enzyme-labeled immunological complex of the ligand with the enzyme-labeled receptor, and B. after separation of uncomplexed enzyme-labeled receptor from the complex, detecting the presence of either the uncomplexed enzyme-labeled receptor or the enzyme-labeled complex as an indication of the presence of the ligand.

Alternatively, a method for the determination of an immunologically reactive ligand comprises:

detecting the presence or amount of either an uncomplexed enzyme-labeled receptor for an immunologically reactive ligand of interest or an enzyme-labeled complex of the enzyme-labeled receptor formed with the ligand, after the ligand is contacted with the buffered composition described above wherein the enzyme-labeled immunoreactant is a receptor for the ligand, and after uncomplexed receptor is separated from any complex formed between the ligand and enzyme-labeled receptor.

Further, a method for the substantial elimination of background in an assay for the determination of an immunologically reactive ligand comprises:

detecting the presence or amount of either an uncomplexed enzyme-labeled receptor for an immunologically reactive ligand of interest or an enzyme-labeled complex of the enzyme-labeled receptor formed with the ligand, after the ligand is contacted with the buffered composition described above wherein the enzyme-labeled immunoreactant is a receptor for the ligand, and after uncomplexed receptor is separated from any complex formed between the ligand and enzyme-labeled receptor.

This invention also provides an enzyme immunoassay employing antibodies or antigens conjugated with an enzyme to form enzyme conjugates for detecting the presence or amount of a ligand in a specimen, the immunoassay comprising addition of a buffered composition comprising: a conjugate of an enzyme and an immunoreactant which is specifically reactive with the ligand or with a receptor therefor, and a heme-containing protein, but the composition excluding 4'-hydroxyacetanilide.

The assay of this invention is not only rapid and accurate, especially for the detection of chlamydial and gonococcal antigens (thus having the advantages of the invention described and claimed in U.S. Ser. No. 522,444, noted above), it has further advantages. The use of the heme-containing protein in admixture with the enzyme-labeled immunoreactant stabilizes the immunoreactant so that background dye formation is no longer a problem.

DETAILED DESCRIPTION OF THE INVENTION

Figure 1:
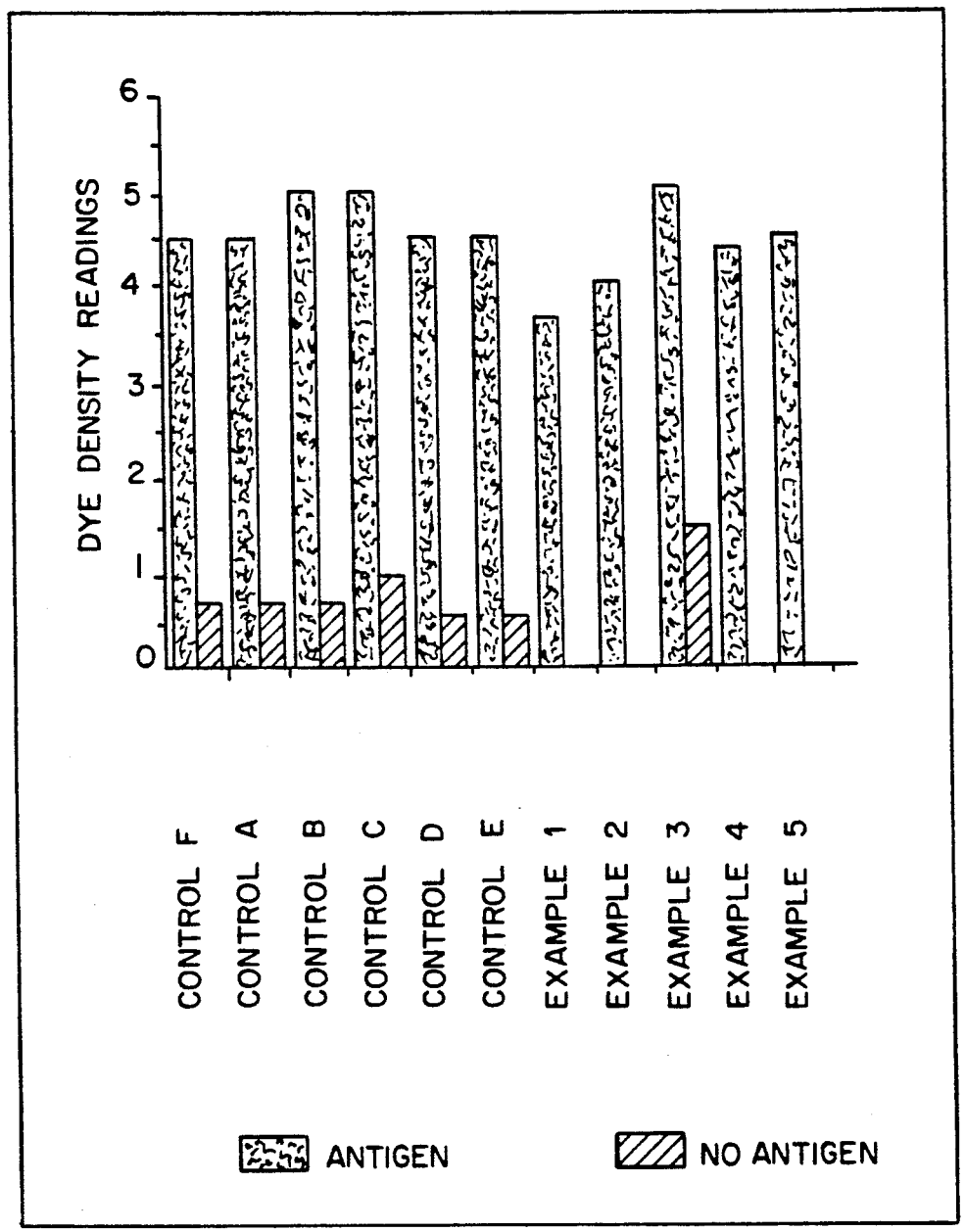
FIG. 1 shows the dye density signals obtained in using several buffered compositions of this invention. It is discussed in detail in Examples 1-5 below.

The present invention provides a very useful composition containing an enzyme-labeled immunoreactant (defined above) which can be used in a variety of immunological assays.

The composition can be used to detect a number of immunological ligands in test specimens to which there are naturally occurring or manufacturable specific binding receptors. The enzyme-labeled immunoreactant of the composition can be directly and specifically reactive with the ligand, or alternatively, reactive with another biological or chemical compound which is specifically reactive with the ligand. The determination of the ligand can be quantitative or qualitative or both.

In particular, the composition of this invention can be used to assay biological fluids of animals, humans or plants, but preferably the fluids of humans. Such fluids include, but are not limited to, whole blood or a component thereof, lymph, bile, urine, spinal fluid, seminal fluid, lacrimal fluid, vaginal secretions, sputum, perspiration, stool specimen, tissue specimens and swab specimens.

Representative ligands which can be detected using the present invention include, but are not limited to, amines, amino acids, peptides, polypeptides, proteins, lipoproteins, glycoproteins, drugs, haptens, enzymes, steroids, hormones (such as human chorionic gonadotropin), vitamins, polysaccharides, glycolipids, alkaloids, organisms or components thereof (such as Streptococcal, Chlamydial or Gonococcal organisms, fungi, molds, protozoa and viruses such as herpes and retroviruses), blood components, tissue and organ antigens. The invention is particularly useful for the detection of antigens extracted from chlamydial or gonococcal organisms. Thus, most of the remainder of this disclosure will be directed to those organisms, but it is to be understood that the invention is not limited to just those preferred embodiments.

The present invention is preferably useful as a method for determining the presence of *C. trachomatis* (or other chlamydial species), or the presence of *N. gonorrhoeae* (or other gonococcal species) in a biological specimen which has been obtained from a patient using any suitable medical or diagnostic techniques. Such specimens include, for example, swab specimens obtained from the cervix, urethra, throat or anus of a patient, and body fluids such as synovial fluid or fluid from lesions. The biological specimens so obtained are suspected of containing bacterial organisms which comprise the chlamydial or gonococcal antigen (or mixture thereof) to be determined.

While the assay can be carried out to detect antigens from intact chlamydial or gonococcal organisms, it is usually desirable to extract the antigens from the organisms in order to increase assay sensitivity. Standard techniques can be used for lysing the organism to release antigen including, for example, solvent dilution or high pH lysing solutions, heating, enzyme treatment and physical agitation such as sonication or centrifugation. The use of anionic detergents or salts such as sodium dodecyl sulfate and deoxycholate is also known.

In the most preferred embodiment, the present invention can be used to detect the chlamydial lipopolysaccharide (glycolipid group) antigen (which is described, for example, in EP-A-0 193 431, published Sep. 3, 1986). In an alternative embodiment, the detected antigen can be the chlamydial major outer membrane protein of the organism which comprises about 60% of the total associated outer membrane protein. This antigen and methods of extraction are described in U.S. Pat. No. 4,427,782 (issued Jan. 24, 1984 to Caldwell et al). In some instances, a mixture of these chlamydial antigens will be detected using a mixture of immunoreagents in the practice of the present invention. In still other embodiments, the invention is used to detect one or more gonococcal antigens (IA or IB protein), or mixtures of antigens from one or more gonococcal strains.

A preferred extraction composition is shown in Examples 1-5 below. That composition contains an alcoholamine or salt thereof and has high pH. In addition, it may be desirable to use a protease in the extraction procedure to break down whole blood and mucus. This is also described in Examples 1-5.

Once antigen is extracted from the organism, it is desirable, although not essential, that the specimen be prefiltered to remove cell debris, particulate matter and other unwanted materials prior to further handling. Prefiltering can be carried out in a suitable container having a filter of some type.

Extraction can be carried out in any suitable container, including devices specially designed for extraction of antigen. Useful devices are known in the art, including U.S. Pat. No. 4,746,614 (issued May 24, 1988 to Devaney, Jr. et al).

Extracted antigen is contacted with a microporous membrane generally having an average pore size of from about 1 to about 10 $\mu$meter, and preferably of about 5 $\mu$meter. The membrane can be prepared from any suitable material that will maintain its integrity during the assay, including but not limited to, sintered glass, porous cellulosic materials, porous polymeric films and filter materials, woven fibers, and others known in the art. Preferably, the membrane is prepared from a polyamide, that is a long-chain synthetic polymer having recurring amide groups in the polymer backbone. They are generally copolymers of a diamine and a dicarboxylic acid, or homopolymers of a lactam of an amino acid. Representative materials include, but are not limited to, polyhexamethylene dodecanediamide (nylon 612), polyhexamethylene adipamide (nylon 66), poly-$\epsilon$-caprolactam (nylon 6), polyhexamethylene sebacamide (nylon 610) and poly-7-aminoheptaneamide (nylon 7), and mixtures thereof. Polyhexamethylene adipamide (nylon 66) is preferred. The membranes are preferably nonionic, although membranes having ionic charges can also be used, if desired. It is essential, however, that the membranes be substantially free of any biological compound reactive with the chlamydial or gonococcal antigen.

Further details of useful membrane materials and of their preparation are found in various published sources including U.S. Pat. No. 4,340,479 (issued Jul. 20, 1982 to Pall) and Pall Corp. trade literature brochures PSD-750a (March 1983, pp. 1-20) and NM-900c (September 1984, pp. 1-28). Useful membranes are also described in U.S. Ser. Nos. 255,920 and 255,923 (noted above). A preferred polyamide microporous membrane is the nylon 66 membrane manufactured and sold by Pall Corp. as BIODYNE TM A or LOPRODYNE TM microporous membranes.

In the practice of this invention, the membrane optionally can be coated or treated with one or more surfactants in an amount of at least about 20 mg/m$^2$. Useful surfactants include, but are not limited to, anionic, amphoteric or nonionic surfactants, with nonionic surfactants being preferred. There are many useful surfactants, and a worker skilled in the art can consult the standard resource, *McCutcheon's Emulsifiers and Detergents*, 1986 Ed., McCutcheon Division Publishing Co., Glen Rock, N.J. to find useful surfactants.

The microporous membrane described herein can be used in combination with other equipment (bottles, test tubes, swabs, beakers or cups) in order to carry out the assay. Alternatively and preferably, it is fitted into a disposable test device in which the assay can be carried out and all fluids accommodated. Useful configurations of test devices are known in the art including U.S. Pat. No. 3,825,410 (issued Jul. 23, 1974 to Bagshawe), U.S. Pat. No. 3,888,629 (issued Jun. 10, 1975 to Bagshawe), U.S. Pat. No. 3,970,429 (issued Jul. 20, 1976 to Updike) and U.S. Pat. No. 4,446,232 (issued May, 1984 to Liotta). Particularly useful devices are described in U.S. Pat. Nos. 4,833,087 (issued May 23, 1989 by Hinckley) and 98,248 (filed Sep. 18, 1987 by Hinckley) which was abandoned in favor of CIP U.S. Ser. No. 240,179 (filed Sep. 6, 1988) now U.S. Pat. No. 4,921,677 (issued May 1, 1990).

Almost immediately upon contact of the antigen with the microporous membrane, the antigen is bound thereto. The antigen is preferentially bound to the membrane as opposed to other proteins, cell components, whole blood or mucus or other debris which may be present in the test specimen or reagents used in the assay.

Within about 5 minutes, and preferably within 1 to 5 minutes, of the contact, unbound materials are separated from the bound antigen, and the bound antigen is contacted with a buffered composition of this invention containing an immunoreactant which will complex with the antigen so as to form an immunological complex bound directly to the support. Fluid and unbound materials may be removed prior to or simultaneously with this contact. A separate wash solution (described below) may be used if desired. If the assay is carried out using a disposable test device, fluid and unbound materials (such as whole blood and mucus components) in the specimen are allowed to flow through the membrane and collected in a suitable compartment during the time the antigen is bound to the membrane.

The buffered composition of this invention includes a suitable enzyme-labeled immunoreactant (antibody, anti-antibody, antigen such as lipopolysaccharide, protein or other material reactive with antibodies, hapten and others described above). This immunoreactant would generally be considered a receptor for the ligand to be detected, as defined above, or a receptor for another receptor molecule. Preferably, the immunoreactant is an enzyme-labeled antibody or fragment thereof (either monoclonal or polyclonal). In a most preferred embodiment, the labeled immunoreactant is an antibody fragment, such as an F(ab')$_2$ fragment. Such labeled fragments and the details of their preparation and use are described in more detail in copending U.S. Ser. No. 522,444 (of Mauck et al, noted above).

A preferred method for preparing antibody fragments and labeling them with an enzyme, such as peroxidase, is described below in relation to the examples. The preferred antibody fragment used in this invention is specifically immunoreactive with one or more chlamydial or gonococcal strains (depending upon what organism is of interest).

The composition can include a plurality of enzyme-labeled immunoreactants (such as F(ab')$_2$ fragments), each directed to one or more ligands of interest. This may be particularly useful where an organism to be detected is found in specimens in a variety of strains.

The immunoreactants are labeled with any suitable enzyme for which a substrate is available in producing a detectable signal in the assay. Useful enzyme labels include, but are not limited to, peroxidase, alkaline phosphatase, acid phosphatase, $\beta$-galactosidase, glucoamylase, glucose oxidase, acetylcholineesterase, catalase, lysozyme, malate dehydrogenase, glucose-6-phosphate dehydrogenase and $\beta$-amylase. Peroxidase and alkaline phosphatase are preferred with peroxidase being most preferred.

Immunoreactants can be labeled with the enzymes using any of a number of known procedures. Antibodies, for example, can be labeled to form enzyme-antibody conjugates using the teaching of Yoshitake et al, *Eur. J. Biochem.*, 101, pp. 395–399 (1979) and Chen et al, *Clin. Chem.*, 30(9), p. 1447 (1984). Antigenic and haptens can be similarly labeled and literature describing such procedures are well known (for example, enzyme-labeled hydantoin derivatives are described in U.S. Pat. No. 4,752,568, issued Jun. 21, 1988 to Danielson et al). Antibody fragments can be labeled with an appropriate enzyme as described for example in U.S. Pat. No. 4,361,647 (issued Nov. 30, 1982 to Remington et al), U.S. Pat. No. 4,810,638 (issued Mar. 7, 1989 to Albaella et al) and Engvall et al, *J. Immunol.*, 109, pp. 129–35, 1972 (one step glutaraldehyde method). Another procedure is described by Imagawa et al, *J. Appl. Biochem.*, 4, pp. 51–57 (1982).

In a preferred method for labeling the F(ab')$_2$ fragment, the fragment is reacted with succinimidyl-4-(N-maleimidomethyl)cyclohexane-1-carboxylate to provide a F(ab')$_2$ fragment reagent. An enzyme, for example peroxidase, is reacted with S-acetylmercaptosuccinic anhydride to provide an enzyme reagent containing a reactive mercapto moiety. This moiety is then reacted with the F(ab')$_2$ reagent to provice the desired enzyme-labeled immunoreagent for use in the assay of this invention. Further details of this procedure are provided in relation to the examples below.

The enzyme-labeled immunoreactants is included in the composition of this invention which is buffered generally to a pH of from about 6 to about 8. Any of a number of readily available buffers can be used including, but not limited to, phosphates, borates, phosphate buffered saline solution, tris(hydroxymethyl)aminomethane, N-tris(hydroxymethyl)methyl-3-aminopropanesulfonic acid and N-tris(hydroxymethyl)methyl-2-aminoethanesulfonic acid.

Also included in this composition is one or more heme-containing proteins. These materials are proteins containing one or more iron atoms conjugated thereto, and include but are not limited to, cytochrome, myoglobin, hemoglobin, hematin, heme, hemin or a mixture of any of these. As used herein, the term "cytochrome" refers to any of a number of proteins conjugated to an iron porphyrin, and which can be obtained from a variety of biological sources. The term includes, but is not limited to, all forms of cytochrome b, cytochrome c, cytochrome f, cytochrome p and others currently known or to be discovered in the future. The term can be used to refer to a single iron-containing protein or to a mixture of such proteins. Myoglobin and cytochrome c are preferred in the practice of this invention with cytochrome c being most preferred. Heme-containing proteins are generally available commercially from a number of sources including Sigma Chemical Co.

In the composition, the heme-containing protein is generally present in a weight ratio to the enzyme-labeled immunoreactant of from about 500:1 to about 10:1. Preferably, this weight ratio is from about 200:1 to about 50:1.

The composition of this invention does not contain 4'-hydroxyacetanilide, a phenolic electron transfer agent, as is used in some known immunological compositions, such as those described in copending U.S. Ser. No. 522,444 (of Mauck et al, noted above).

Optional, but preferred, components of the composition include one or more nonimmunological proteins which reduce nonspecific interactions in an assay. By "nonimmunological proteins" is meant proteins which do not bind in an immunological reaction with the antigen of interest to an appreciable extent. Useful nonimmunological proteins are well known and include, for example, casein, $\alpha$-casein, fetal bovine serum and porcine gamma globulin.

Another optional but preferred component is an amphoteric surfactant, as described in copending U.S. Ser. No. 255,925 (filed Oct. 7, 1988 by Pronovost) now U.S. Pat. No. 5,047,326 (issued Sep. 10, 1991.

In the preferred assay of this invention, once the bound antigen has been contacted with the buffered composition containing the labeled immunoreactant, a bound immunological complex is formed on the membrane almost immediately. To hasten the formation of this complex, the membrane and reagents can be incubated at a temperature of from about 15 to about 30° C. for up to 10 minutes. Preferably, the incubation is carried out at from about 18° to about 25° C. (that is, room temperature) for from 1 to 3 minutes. These mild incubation conditions are in sharp contrast to the 30 minutes at 37° C. described as necessary for absorption of chlamydial antigen to bare supports in U.S. Pat. No. 4,497,899 (noted above).

After this incubation and within about 10 minutes (preferably within 1 to 3 minutes) of the beginning of complex formation, the bound complex is washed one or more times with a wash solution which generally has a pH of from about 7 to about 12. Such a wash solution can be used one or more times at any time in the assay. The solution preferably contains one or more surfactants to aid in separating unbound materials from the bound complex. Particularly useful surfactants are cationic surfactants, as described in U.S. Ser. No. 255,924 (filed Oct. 7, 1988 Pronovost et al) now U.S. Pat. No. 5,047,325 (issued Sep. 10, 1991.

After the washing, the bound labeled complex is appropriately detected. Generally, in order to detect the bound labeled complex on the microporous membrane, an appropriate dye-providing composition is contacted with the complex. This composition contains a substrate for the enzyme so the enzyme directly or indirectly provides a detectable dye if the enzyme is present. The dye can be a single compound which is activated by enzymatic action, or it can be formed from the enzymatic action of two or more compounds, or from an intermediate formed from two or more compounds. Appropriate substrates would be readily apparent to one of ordinary skill in the art.

In a particularly preferred embodiment, the enzyme label is peroxidase, and at some point in the assay, hydrogen peroxide and a suitable dye-providing composition is added to provide a detectable dye. For example, useful dye-providing reagents include leuco dyes, such as triarylimidazole leuco dyes (as described in U.S. Pat. No. 4,089,747, issued May 16, 1978 to Bruschi), or other compounds which react to provide a dye in the presence of peroxidase and hydrogen peroxide (that is, compounds which react to provide a dye upon catalytic action of peroxidase).

Addition of the dye-providing composition is done relatively quickly after washing the bound complex, that is generally within about 2 minutes, and preferably immediately thereafter. If desired, dye detection can be hastened with incubation if the reagents warrant it. The resulting dye is then detected using standard equipment and procedures to make visual or spectrophotometric readings.

Representative of the preferred embodiment of this invention is a method for the determination of a chlamydial or gonococcal antigen in a biological specimen comprising:

A. contacting antigen extracted from Chlamydial or Gonococcal organisms suspected of being present in a biological specimen with a microporous membrane to bind the antigen thereto, B. contacting the bound antigen with a buffered composition comprising an enzyme-labeled antibody or fragment thereof directed to the antigen, the enzyme-labeled antibody or fragment thereof being in admixture with a heme-containing protein, but the composition excluding 4'-hydroxyacetanilide, so as to form an enzyme-labeled immunological complex between the antigen and the enzyme-labeled antibody or fragment thereof bound to the membrane, C. contacting the bound complex with a composition which provides a dye in the presence of the enzyme, and D. detecting the presence of the dye on the membrane as an indication of the presence or amount of the Chlamydial or Gonococcal organisms in the specimen.

An alternative, but not preferred, immunoassay of this invention is carried out similarly to the preferred method described above, except that the antibody (or fragment thereof) directed to the antigen of interest is not labeled. Thus, an unlabeled complex is formed which is bound to the membrane (or other suitable substrate). After separating the bound complex from unbound materials (such as by washing), the bound complex is contacted with a buffered composition of this invention containing a heme-containing protein and an enzyme-labeled immunoreactant directed to either the antigen or antibody of the bound complex. Generally, the labeled immunoreactant is an antibody directed to the complexed antibody. Thus, it is an enzyme-labeled anti-antibody. Example 7 below illustrates this embodiment in the direction of a chlamydial antigen.

Thus, an example of this embodiment is a method for the determination of a chlamydial or gonococcal antigen in a biological specimen comprising:

A. contacting antigen extracted from Chlamydial or Gonococcal organisms suspected of being present in a biological specimen with a microporous membrane to bind the antigen thereto, B. contacting the bound antigen with an unlabeled antibody or fragment thereof directed to the antigen, so as to form an unlabeled immunological complex between the antigen and the unlabeled antibody or fragment thereof bound to the membrane, C. contacting the bound complex with a buffered composition comprising an enzyme-labeled anti-antibody or fragment thereof directed to the unlabeled antibody, the enzyme-labeled anti-antibody or fragment thereof being in admixture with a heme-containing protein, but the composition excluding 4'-hydroxyacetanilide, so as to form an enzyme-labeled immunological complex among the antigen, unlabeled antibody and enzyme-labeled anti-antibody bound to the membrane, D. contacting the bound complex with a composition which provides a dye in the presence of the enzyme, and E. detecting the presence of the dye on the membrane as an indication of the presence or amount of the organisms in the specimen.

Still other embodiments of this invention include the use of the buffered composition of this invention in competitive binding assays, enzyme-linked immunosorbent assays (ELISA) and immunometric assays ("sandwich") wherein an enzyme-labeled immunoreactant is used to bind to either the ligand of interest or to a receptor therefor. The enzyme-labeled immunoreactant then can provide a means for detecting either complexed or uncomplexed ligand in the assay using suitable substrates and dye-providing compositions, and thus give an indication of the presence (or absence) or amount of the ligand (or mixture of ligands) in a test sample. The details of how to carry out such assays are well known in the art, and considerable literature has been published so that it is unnecessary to cite anything more than an representative sampling of such documents: U.S. Pat. No. 3,654,090 (issued Apr. 4, 1972 to Schuurs et al, U.S. Pat. No. 4,016,043 (issued Apr. 5, 1977 to Schuurs et al), U.S. Pat. No. 4,486,530 (issued Dec. 4, 1984 to David et al), U.S. Pat. No. 4,670,381 (issued Jun. 2, 1987 to Frickey et al), U.S. Pat. No. 4,520,113 (issued May 28, 1985 to Gallo et al), GB-A-2,074,747 (published Nov. 4, 1981), EP-A-0 109 012 (published May 23, 1984) and WO-A-87/03690 (published Jun. 18, 1987). Example 8 below, however, is illustrative of a sandwich assay for hCG (human chorionic gonadotropin).

The diagnostic test kit of the present invention comprises the immunological composition described herein and one or more other component compositions, solutions or devices for carrying out the assay. For instance, it generally includes the buffered composition of this invention, and an appropriate dye-providing composition in a separate container. Optional components of the kit include wash solutions, extraction compositions, extraction devices, swabs or other specimen collecting means, disposable test devices (including a microporous membrane fitted therein) and others known to one skilled in the art, all in appropriate packages or containers.

The following examples are provided to illustrate, but not limit the scope of, the present invention. All percentages are based on weight unless otherwise indicated.

Materials

The antibodies used in preparing the F(ab')$_2$ anti-chlamydial fragment were 10G9 monoclonal antibodies directed to the chlamydial lipopolysaccharide antigen obtained from Cetus Corp. (Emeryville, Calif.) in a phosphate buffered saline solution (6.96 mg/ml, pH 7.2).

Pepsin was obtained from Sigma Chemical Co. (catalog no. 6887, 3900 units/mg of protein).

The following materials were also commercially obtained: succinimidyl-4-(N-maleimidomethyl)cyclohexane-1-carboxylate (Pierce Chemical Co.), S-acetylmercaptosuccinic anhydride (Aldrich Chemical Co.), horseradish peroxidase (Miles Laboratories), Amicon concentrator (Amicon, Danvers, Mass.), ABx column (J. T. Baker, Phillipsburg, N.J.), PD-10 column (Pharmacia) and DEAE-Sepharose column (Waters, Milford, Mass.). The other materials were obtained from Eastman Kodak Company.

Preparation of Antibody Fragment

A phosphate buffered saline solution (14 ml) of the anti-chlamydial antibody (6.96 mg/ml) was dialyzed using an Amicon concentrator with a 30,000 molecular weight cutoff membrane and citrate buffer (56 ml, 0.1 molar, pH 4.1). The final volume was 9 ml containing 10.8 mg/ml of citrate buffer. This solution was mixed with pepsin (1.169 ml of a solution containing 2.5 mg/ml of citrate buffer), and the resulting mixture was rotated for two hours at 37° C. The pH was raised to 7 with tris(hydroxymethyl)aminomethane buffer (1 molar, pH 10.8), and the solution was dialyzed using an Amicon concentrator with a 30,000 molecular weight cutoff membrane using tris(hydroxymethyl)aminomethane buffer (20 mmolar, pH 8). The resulting solution (about 30 µl) was stored at 4° C. until use.

This product was purified on a DEAE-Sepharose column using first tris(hydroxymethyl)aminomethane buffer (25-30 ml, 20 mmolar, pH 8), then with the buffer (25 ml) and sodium chloride (0.75 molar). The portions containing the antibody fragments (OD$_{280}$) were pooled and dialyzed against 2-(N-morpholino)-ethanesulfonic acid (25 mmolar, pH 6.5) to give 21.8 mg total of F(ab')$_2$ and F(ab') fragments.

These fragments were separated by chromatography using an ABx column and eluting with 2-(N-morpholino)ethanesulfonic acid (30 ml, 25 mmolar, pH 5.6), followed by a solution (30 ml) consisting of ammonium sulfate (0.5 molar) and sodium acetate (0.02 molar). The fractions containing the F(ab')$_2$ fragment were pooled, combined and dialyzed against phosphate buffered saline solution in an Amicon concentrator to give pure F(ab')$_2$ fragment (13.85 mg).

Preparation of Labeled Fragment

Step A:

Horseradish peroxidase (100 mg dry weight) was dissolved in sodium carbonate (13.4 ml, 0.1 molar pH 9.5) at 4° C. and reacted with a solution of S-acetylmercaptosuccinic anhydride in dry N,N-dimethylformamide (300 µl at 17.4 mg/ml) for one hour at 4° C. or lower. This mixture was transferred by pipette into a SPECTROPOR ™ dialysis bag (available from Spectrum Medical Ind., Los Angeles) that had been prewet with deionized distilled water for 10 minutes. The bag was then placed into phosphate buffered saline solution (pH 7.4) using 50 times the volume of the reaction mixture, and slowly stirred at 4° C. for about four hours. The solution volume was concentrated using an Amicon concentrator to give the desired intermediate (18.6 mg/ml).

The intermediate just prepared (2.61 ml of solution containing 18.6 mg/ml) in phosphate buffered saline solution (pH 7.4) was unblocked by reaction with a solution containing hydroxylamine (0.652 ml, 0.25 molar) in phosphate buffer (0.25 molar, pH 7.5) and ethylenediaminetetraacetic acid (0.001 molar) for two hours at room temperature. The resulting enzyme reagent was purified by chromatography using a PD-10 column and phosphate buffereed saline soultion (pH 7.4) as the eluent.

Step B:

The purified F(ab')$_2$ fragment described above (13.85 mg of a solution of 2.5 mg/ml in phosphate buffered saline solution) was mixed with succinimidyl-4-(N-maleimidomethyl)cyclohexane-1-carboxylate (130.2 µl of 16.7 mg/ml N,N-dimethylformamide) and shaken for two hours at 4° C. The resulting product was purified by chromatography using a PD-10 column and phosphate buffered saline solution (pH 7.4) as the eluent.

Step C:

The enzyme reagent (2.6 ml of a solution of 18.6 mg/ml of phosphate buffered saline solution) prepared in Step A above, and the product (10.5 ml of a solution of 1.32 mg/ml of phosphate buffered saline solution) prepared in Step B were mixed, the concentration was adjusted to about 1 mg/ml of the F(ab')$_2$ fragment, and then the mixture was rotated for about 15 hours at 25° C. The resulting conjugate of enzyme-labeled fragment was dialyzed against 2-(N-morpholino)ethanesulfonic acid buffer (40 µl, 25 mmolar, pH 5.6) using an Amicon concentrator with a 10,000 molecular weight cutoff membrane. The resulting product (5 µl) was then purified using an ABx column, eluting with 15 ml of a solution of 2-(N-morpholino)ethanesulfonic acid, followed by a gradient solution (about 30 ml) of ammonium sulfate (0.5 molar) and sodium acetate (20 mmolar), pH 6.7. Fractions having an absorbance ratio (403/280) of about 0.6 were pooled to give 4.85 mg of the desired peroxidase labeled fragment.

The labeled fragment was stored in a phosphate buffered saline solution (0.2% solution, pH 7.4) containing merthiolate preservative (0.01%) at 4° C. The molecular weight range of the labeled fragment was about 135 to about 250 kdaltons.

EXAMPLES 1-5

Comparison of Buffered Compositions

These examples illustrate several buffered compositions of this invention and their use in direct binding immunoassays for chlamydial antigen. The compositions of this invention are compared to compositions outside the scope of this invention (Controls A-F) in the immunoassays.

Materials

Chlamydial antigen solution comprised chlamydial Serovar G elementary bodies in phosphate buffered saline solution (pH 7.2) containing bovine serium albumin (0.1 mg/ml). A Blank Control solution comprised bovine serum albumin (0.1 mg/ml) in phosphate buffered saline solution (pH 7.2) without antigen.

SURECELL TM disposable test devices (Eastman Kodak Co.) were used containing uncoated Lo-Prodyne TM microporous membranes (5 $\mu$m, Pall Corp.) in each test well.

An extraction tube was used to extract chlamydial antigen from the elementary bodies having at separate locations on the inside thereof, dried coatings of: (1) tris(hydroxymethyl)aminomethane buffer (Sigma Chemical, 20 $\mu$l of a 1.65 molar solution, pH 11) with thimerosal preservative (0.01%), and (2) 2-(N-morpholino)ethane sulfonic acid (10 mmolar, 50 $\mu$l solution, pH 6), sodium azide (1.54 mmolar), ethylenediaminetetraacetic acid (5.4 mmolar), 5,5-dimethyl-1,3-cyclohexanedione (21.4 mmolar), dithiothreitol (188 mmolar) and poly(acrylamide) (6.35%).

Composition 1 contained AMIDECK TM protease (4 mg/ml, 170 units/mg, available from Genencor, International, Rochester, N.Y.) in 10 mmolar 2-(N-morpholino)ethane sulfonic acid buffer (pH 6), sodium chloride (50 mmolar), calcium chloride (5 mmolar), 1,2-propanediol (10% w/v) and thimerosal (0.01%).

An extraction composition contained ethanolamine hydrochloride (0.47 molar), sodium chloride (0.27 molar), thimerosal (30 mmolar) ethylenediaminetetraacetic acid (50 mmolar), EMCOL TM CC-36 cationic surfactant (0.45% from Witco Chemical) and sodium hydroxide (0.66 normal, to provide a pH of 13.5).

Composition 2 contained hydrogen peroxide (12% in water), diethylenetriaminepentaacetic acid (10 $\mu$molar) and thimerosal (0.01%).

A wash solution contained 3-cyclohexylamino-2-hydroxy-1-propanesulfonic acid buffer (0.05 molar, pH 10), EMCOL TM CC-9 cationic surfactant (0.75%) and thimerosal (0.01%).

A dye-providing composition comprised 2-(4-hydroxy-3-methoxyphenyl)-4,5-bis(4-methoxyphenyl)imidazole leuco dye (0.008%), poly(vinyl pyrrolidone) (1%), sodium phosphate (10 mmolar, pH 6.8) diethylenetriaminepentaacetic acid (10 $\mu$molar), 4'-hydroxyacetanilide (2 mmolar) and hydrogen peroxide (10 mmolar).

Five buffered compositions of this invention were prepared by mixing the labeled fragment prepared as described above (4 $\mu$g/ml of solution, final concentration) with a heme-containing protein (0.11 to 1.25 mg/ml, as noted below), casein (0.05%), LONZAINE TM C amphoteric surfactant (0.01%, Lonza Corp.) and thimerosal (0.01%) in phosphate buffered saline solution (pH 7.2). None of these compositions included 4'-hydroxyacetanilide, which is a phenolic electron transfer agent.

Controls A-E were like the buffered compositions of this invention except they further included 4'-hydroxyacetanilide (10 mmolar).

Control F composition was similarly prepared, but contained no heme-containing protein or 4'-hydroxyacetanilide.

Examples 1-5 and Controls A-E contained the following amounts of heme-containing protein:

Example 1 and Control A: 0.125 mg/ml of myoglobin.
Example 2 and Control B: 0.25 mg/ml of myoglobin.
Example 3 and Control C: 1.25 mg/ml of myoglobin.
Example 4 and Control D: 0.11 mg/ml of cytochrome c.
Example 5 and Control E: 0.23 mg/ml of cytochrome c.

Assay Procedure

For each of the Examples and Controls, the following assay procedure was followed.

Composition 1 (8 drops) was added to an extraction tube, followed by the elementary bodies, and mixed for 5-10 seconds. The tube and contents were then incubated for 1 minute at room temperature (18°-25° C.). The extraction composition (8 drops) was added and mixed 5-10 seconds with the tube's contents, then incubated one minute at room temperature. Composition 2 (8 drops) was added, mixed 5-10 seconds, and incubated with the tube's contents for two minutes at room temperature.

The resulting solution containing extracted lipopolysaccharide antigen was removed from the tube using a pipette, prefiltered, and transferred to each well of a SORECELL TM disposable test device (160 $\mu$l containing 500 pg of antigen per well). Fluid was allowed to drain through the microporous membranes in the wells. Each well was then washed twice with the wash solution (250 $\mu$l each), and allowed to drain.

The Blank Control solution was similarly treated with the extraction composition, prefiltered and transferred to each well of specific test devices.

Each labeled fragment composition (either Example or Control, 1 drop each) was then added to test wells (of devices to which antigen had been added, and of devices to which the Blank Solution had been added), followed by incubation at room temperature for two minutes to form an immunological complex on the membrane of each well. The wells were washed three times (250 $\mu$l each) and allowed to drain each time.

The dye-providing composition (2 drops) was added and after three minutes incubation at room temperature, the dye formed on the membranes was evaluated against a graduated color chart having values of 0 to 10, with 0 representing no dye density and 10 representing the highest dye density. The values observed in the test devices (with and without extracted chlamydial antigen) are shown in the FIGURE as the averages of three separate assays for each test. The background signals were observed in the test wells to which no antigen had been added (Blank Control solution).

These results indicate that the compositions of this invention (heme-containing protein, but omitting the 4'-hydroxyacetanilide) gave acceptable signal to background ratios (except for Example 3 which is believed to be an anomaly caused by insufficient washing or membrane variability). However, where 4'-hydroxyacetanilide was present in the composition (Controls A-E), the background was generally too high, as indicated by evaluating the dye density in the test wells to which no antigen had been added. Similar test wells showed no dye where the composition contained a heme-containing protein and 4'-hydroxyacetanilide was omitted.

EXAMPLE 6

Buffered Composition Containing CK-MB Antibody Fragment

Another buffered composition of this invention was prepared by mixing together: creatine kinase-MB F(ab')$_2$ antibody fragment conjugated to horseradish peroxidase (5 μg/ml), casein (0.05%), LONZAINE TM C amphoteric surfactant (0.01% from Lonza Corp.), cytochrome c (0.5 mg/ml) and thimerosal (0.01%) in phosphate buffered saline solution (pH 7.2). The labeled fragment was prepared by the same procedure as described above for the labeled fragments used in Example 1 above. However, the final chromatography was done using a standard DEAE column rather than a standard ABx column. Eluting buffers used were: (1) tris(hydroxymethyl)aminomethane (20 mmolar, pH 8), and (2) tris(hydroxymethyl)aminomethane (20 mmolar, pH 8) containing sodium chloride (0.74 molar).

EXAMPLE 7

Buffered Composition Containing Whole Antibody and Use in Assay

This example demonstrates the use of a buffered composition of this invention in a direct binding assay similar to those of Examples 1-6 except that the buffered composition contains an enzyme-labeled anti-antibody, not labeled antibody.

Materials

Serovar G antigen purified elementary bodies were obtained from Professor W. J. Newhall of Indiana University. Antigen solution (5 μl containing about 2900 ng antigen/μl) was diluted with bovine serum albumin in phosphate buffered saline solution (0.1 mg/ml, pH 7.2) to obtain a final concentration of about 500 pg, which was the amount usually added to each test well of a SURECELL TM test device.

A mouse monoclonal antibody to the chlamydial lipopolysaccharide antigen was prepared using standard hybridoma technology and a standard mouse cell line and stored in a solution of phosphate buffered saline solution (pH 7.2) containing sodium azide (0.01%). An antibody reagent composition was prepared by adding a sample (19 μl) of the antibody solution to a phosphate buffered saline solution (diluting 1:800) containing casein (0.5%) as a blocking protein and LONZAINE TM C amphoteric surfactant (0.01%), then filtered through a 0.22 μmeter filter to obtain a working solution.

A polyclonal goat anti-mouse IgG antibody was conjugated to horseradish peroxidase. This conjugate was diluted to about 1:750 in phosphate buffered saline solution containing casein (0.5%), LONZAINE TM C amphoteric surfactant (0.01%) and cytochrome c (0.5 mg/ml) to form a buffered composition of this invention. It was then prefiltered. A Control composition was similarly prepared but omitting the cytochrome c.

A negative control reagent composition was prepared with creatine kinase-MB antibody (5 μg/ml), casein (0.5%), LONZAINE TM C amphoteric surfactant (0.01%) and thimerosal preservative (0.01%) in phosphate buffered saline solution (pH 7.2).

SURECELL TM disposable test devices (Eastman Kodak Co.) were used containing uncoated LOPRODYNE TM microporous membranes (5 μm, Pall Corp.) in each test well.

Other compositions used in this example were the same as those used in Examples 1-5 above.

Assay Procedure

Eight SURECELL TM disposable test devices were used in this example. Each assay (Example and Control) were carried out twice. Two sets of test devices were used with solutions of extracted antigen, and two sets were carried out without antigen (negative control reagent composition). Each set of tests were carried out with the buffered composition of this invention and with the Control composition (no cytochrome c).

Composition 1 (8 drops) was added to an extraction tube, followed by the addition of the elementary bodies, mixed 5 seconds, then incubated at room temperature for one minute. The extraction composition (8 drops) was added to the tube, the tube's contents mixed for 5 seconds and incubated for one minute at room temperature. Composition 2 (8 drops) was then added to the tube, mixed with the contents for 5 seconds and incubated for 2 minutes at room temperature.

A blank sample (no antigen) was similarly treated.

Samples with and without antigen were removed from the extraction tubes using a pipette, and added to the test wells of separate SURECELL TM test devices (160 μl each containing about 500 pg of antigen where present). After the fluids drained through the membranes, each test well was washed with the wash solution (about 300 μl), and allowed to drain. The unlabeled monoclonal antibody composition (2 drops) was added to a test well of each test device. The control reagent composition (2 drops) was added to another test well of each device. After incubation of the test devices for 2 minutes at room temperature, each test well was washed using the wash solution (about 300 μl).

The buffered composition of this invention containing cytochrome c (2 drops) was added to all test wells of one set of test devices. The Control buffered composition (2 drops) was similarly added to another set of test devices. After incubating all test devices for five minutes at room temperature, the test wells were washed twice with the wash solution (about 300 μl each time). The dye-providing composition (2 drops) was then added and the test devices were incubated for another five minutes at room temperature. The dye density was evaluated as described in Examples 1-5.

The results of these evaluations indicated that the assay of this invention carried out using the buffered composition containing cytochrome c gave a visual dye density of about 4 with no background. The assay carried out using the Control buffered composition gave a dye density between 4 and 5, but the background was an unacceptable 0.5.

EXAMPLE 8

Assay for Human Chorionic Gonadotropin

This example demonstrates the practice of the present invention to detect hCG using a sandwich assay and a buffered composition of this invention.

Materials

SURECELL TM disposable test devices were used containing LOPRODYNE TM microporous membranes (5 μm, Pall Corp.), each coated with FLUO-RAD TM FC 135 nonionic surfactant (3M, 0.05 g/m$^2$).

Affinity purified goat anti-hCG alpha polyclonal antibodies (OEM Concepts, Toms River, N.J.) were bound to derivatized styrene beads. A composition (2 μl) comprising the beads (0.9%), polyacrylamide (5%), UVITEX TM dye (0.01%) and thimerosal preservative (0.01%) in glycine buffer (0.1 molar, pH 8.5) was deposited on a finite area of the membrane in one of the test wells (designated the sample well).

Goat gamma globulin was bound to the same type of beads and deposited onto the membrane in another test well (designated the negative control well). A third test well (designated the positive control well) contained anti-hCG antibodies bound to beads and hCG antigen prebound to the antibodies.

The test solution contained hCG (50 mI.U./ml) in a solution of phosphate buffered saline solution (150 mmolar sodium chloride, 50 mmolar sodium phosphate, pH 6.2), bovine serum albumin (0.7%) and merthiolate (0.01%).

A conjugate of anti-hCG monoclonal antibodies (Cambridge Medical Diagnostics) and horseradish peroxidase (Miles) was prepared using the procedures described by Yoshitake et al, *Eur. J. Biochem.*, 101, 395 (1979). This conjugate was mixed with 2-(4-morpholino)ethanesulfonic acid buffer (4.88%), cytochrome c (0.05%), bovine serum albumin (1%) and thimerosal (0.01%) to form a buffered composition of this invention.

A wash solution was prepared from sodium phosphate (0.1 molar, pH 7.2), sodium decyl sulfate (100 mmolar, 2.7%), sodium chloride (0.3 molar) and thimerosal (0.01%).

A dye-providing composition comprised 2-(4-hydroxy-3-methoxyphenyl)-4,5-bis(4-methoxyphenyl)imidazole leuco dye (0.005%), poly(vinyl pyrrolidone) (1%), sodium phosphate buffer (5 mmolar, pH 6.8) diethylenetriaminepentaacetic acid (10 μmolar), 4'-hydroxyacetanilide (2 mmolar) and hydrogen peroxide (10 mmolar).

Assay Procedure

The test solution (150 μl) containing hCG (50 mI.U./ml) was added to the three test wells of the test device, and the fluids were allowed to drain through the membranes. The buffered composition containing labeled antibody (1 drop, about 40 μl) was added to each test well, and allowed to drain through. The test wells were washed twice (each time with 300 μml) and allowed to drain through. The dye-providing composition (50 μl) was then added to each test well and allowed to drain through. After a brief incubation at room temperature, the dye density on the membranes was evaluated and scored against a color chart as described in Examples 1-5 above. The areas around the applied compositions in the test wells were evaluated as background. The assay was carried out three times.

The results are provided in the following table as visual dye densities seen in the specific test wells for each of the three tests:

TABLE

| Negative Control Well | | Sample Well | | Positive Control Well | |
|---|---|---|---|---|---|
| Test | Background | Test | Background | Test | Background |
| 0 | 0 | 1-2 | 0 | 7 | 0 |
| 0 | 0 | 2 | 0 | 7 | 0 |
| 0 | 0 | 2 | 0 | 7 | 0 |

These data show that in three separate assays, a very low concentration of hCG (50 mI.U.) can be readily detected with zero background.

The invention has been described in detail with particular reference to preferred embodiments thereof, but it will be understood that variations and modifications can be effected within the spirit and scope of the invention. Moreover, all patents, patent applications (published or unpublished, foreign or domestic), literature references or other publications noted above are incorporated herein by reference for any disclosure pertinent to the practice of this invention.

We claim:

1. A test kit useful for the determination of an immunologically reactive ligand, said kit comprising, in individual packaging:
   a. a buffered composition comprising a water-soluble, non-particulate enzyme-labeled immunoreactant in admixture with a heme-containing protein which reduces background in enzyme label immunoassays, but said composition excluding 4'-hydroxyacetanilide, said immunoreactant being a receptor for said ligand, said heme-containing protein and said immunoreactant being present in said composition at a weight ratio of from about 500:1 to about 10:1, and
   b. a dye-providing composition which provides a dye in the presence of said enzyme label.

2. The test kit of claim 1 wherein said immunoreactant is an antibody or F(ab')$_2$ fragment thereof.

3. The test kit of claim 2 wherein said antibody or F(ab')$_2$ fragment thereof specifically binds to either a chlamydial antigen or to human chorionic gonadotropin.

4. The test kit of claim 1 wherein said immunoreactant is labeled with peroxidase, alkaline phosphatase, acid phosphatase, β-galactosidase, glucoamylase, glucose oxidase, acetylcholineesterase, catalase, lysozyme, malate dehydrogenase, glucose-6-phosphate dehydrogenase or β-amylase, and said heme-containing protein is cytochrome, myoglobin, hemoglobin, hematin, heme, hemin or a mixture of any of these.

5. The test kit of claim 4 wherein said immunoreactant is labeled with peroxidase, said dye-providing composition comprises a triarylimidazole leuco dye which provides a dye in the presence of peroxidase and hydrogen peroxide, and said heme-containing protein is cytochrome c.

6. The test kit of claim 1 further comprising a disposable test device including a microporous membrane fitted therein.

7. A method for the determination of an immunologically reactive ligand comprising:

A. contacting an immunologically reactive ligand of interest with a buffered composition comprising a water-soluble, non-particulate enzyme-labeled receptor for said ligand, said enzyme-labeled receptor being in admixture with a heme-containing protein which reduces background in immunoassays, but said composition excluding 4'-hydroxyacetanilide, said heme-containing protein and said enzyme-labeled receptor being present in said composition at a weight ratio of from about 500:1 to about 10:1, so as to form an enzyme-labeled immunological complex of said ligand with said enzyme-labeled receptor, and B. after separation of uncomplexed enzyme-labeled receptor from said complex, detecting the presence of either said uncomplexed enzyme-labeled receptor or said enzyme-labeled complex as an indication of the presence of said ligand.

8. The method of claim 7 wherein said ligand is either a chlamydial or gonococcal antigen or human chorionic gonadotropin and said enzyme-labeled receptor is an antibody of $F(ab')_2$ fragment thereof that specifically bind to said chlamydial or gonococcal antigen or human chorionic gonadotropin, respectively.

9. The method of claim 8 wherein said enzyme-labeled receptor is a peroxidase-labeled $F(ab')_2$ antibody fragment, and said heme-containing protein is cytochrome, myoglobin, hemoglobin, hematin, heme, hemin or a mixture of any of these.

10. A method for the determination of a chlamydial or gonococcal antigen in a biological specimen comprising:

A. contacting antigen extracted from chlamydial or gonococcal organisms suspected of being present in a biological specimen with a microporous membrane to bind said antigen thereto, B. contacting said antigen bound with a buffered composition comprising a water-soluble non-particulate enzyme-labeled antibody or $F(ab')_2$ fragment thereof which specifically binds to said antigen, said enzyme-labeled antibody or $F(ab')_2$ fragment thereof being in admixture with a heme-containing protein, but said composition excluding 4'-hydroxyacetanilide, so as to form an enzyme-labeled immunological complex between said antigen and said enzyme-labeled antibody or $F(ab')_2$ fragment thereof bound to said membrane, C. contacting the bound complex with a composition which provides a dye in the presence of said enzyme, and D. detecting the presence of said dye on said membrane as an indication of the presence or amount of said chlamydial or gonococcal organisms in said specimen.

11. The method of claim 10 wherein said chlamydial antigen is contacted with a peroxidase-labeled antibody or $F(ab')_2$ fragment thereof which binds thereto in admixture with a heme-containing protein which is cytochrome, myoglobin, hemoglobin, hematin, heme, hemin or a mixture of any of these, and said dye-providing composition comprises a triarylimidazole leuco dye which provides a dye in the presence of peroxidase and hydrogen peroxide.

12. A method for the determination of an immunologically reactive ligand comprising:

detecting the presence or amount of either an uncomplexed water-soluble, non-particulate enzyme-labeled receptor for an immunologically reactive ligand of interest or an enzyme-labeled complex of said enzyme-labeled receptor bound to said ligand, after said ligand is contacted with a buffered composition comprising said enzyme-labeled receptor in admixture with a heme-containing protein, but said composition excluding 4'-hydroxyacetanilide, and after uncomplexed receptor is separated from any complex formed between said ligand and enzyme-labeled receptor.

13. A method for the substantial elimination of background in an assay for the determination of an immunologically reactive ligand, said method comprising:

detecting the presence or amount of either an uncomplexed, water-soluble, non-particulate enzyme-labeled receptor for an immunologically reactive ligand of interest or an enzyme-labeled complex of said enzyme-labeled receptor bound to said ligand, after said ligand is contacted with a buffered composition comprising said enzyme-labeled receptor in admixture with a heme-containing protein which reduces background in said assay, but said composition excluding 4'-hydroxyacetanilide, said heme-containing protein and said enzyme-labeled receptor being present in said composition at a weight ratio of from about 500:1 to about 10:1, and after uncomplexed receptor is separated from any complex formed between said ligand and enzyme-labeled receptor, said heme-containing protein selected from the group consisting of cytochrome c, myoglobin, hemoglobin, hematin, heme, hemin and a mixture of any of these.

14. In an enzyme immunoassay employing antibodies or antigens conjugated with an enzyme to form enzyme conjugates for detecting the presence or amount of a ligand in a specimen, wherein the improvement comprises adding a buffered composition to a specimen, said composition comprising: a water-soluble, non-particulate conjugate of an enzyme and an immunoreactant which is specifically reactive with said ligand or with a receptor therefor, and a heme-containing protein which reduces background in said enzyme immunoassay, but said composition excluding 4'-hydroxyacetanilide, said heme-containing protein and said conjugate being present in said composition at a weight ratio of from about 500:1 to about 10:1.

15. A method for the determination of a chlamydial or gonococcal antigen in a biological specimen comprising:

A. contacting antigen extracted from chlamydial or gonococcal organisms suspected of being present in a biological specimen with a microporous membrane to bind said antigen thereto, B. contacting antigen bound to said membrane with an unlabeled antibody of $F(ab')_2$ fragment thereof directed to said antigen, so as to form an unlabeled immunological complex between said antigen and said unlabeled antibody or $F(ab')_2$ fragment thereof bound to said membrane, C. contacting said complex bound to said membrane with a buffered composition comprising a water-soluble, non-particulate enzyme-labeled anti-antibody or $F(ab')_2$ fragment thereof directed to said unlabeled antibody, said enzyme-labeled anti-antibody of F(ab')$_2$ fragment thereof being in admixture with a heme-containing protein which reduces background in enzyme label immunoassays, but said composition excluding 4'-hydroxyacetanilide, said heme-containing protein and said labeled anti-antibody or F(ab')$_2$ fragment thereof being present in said composition at a weight ratio of from about 500:1 to about 10:1.

so as to form an enzyme-labeled immunological complex among said antigen, unlabeled antibody and enzyme-labeled anti-antibody bound to said membrane, D. contacting said complex bound to said membrane composition which provides a dye in the presence of said enzyme-labeled anti-antibody, and E. detecting the presence of said dye on said membrane as an indication of the presence or absence of said organisms in said specimen.

* * * * *